(12) United States Patent
Lahiri et al.

(10) Patent No.: US 8,513,427 B2
(45) Date of Patent: Aug. 20, 2013

(54) COMPOUNDS FOR PRODUCING SUBSTITUTED SULFOXIDES, PROCESS FOR PRODUCING THE SAME AND USE THEREOF

(75) Inventors: Saswata Lahiri, Secunderabad (IN); Lakshmana Rao Vadali, Secunderabad (IN); Swamy Saidugari, Secunderabad (IN); Verra Narayana Bandlamudi, Secunderabad (IN); Parameshwar Makam, Secunderabad (IN); Seshadri Rao Manukonda, Secunderabad (IN); Debashish Datta, Secunderabad (IN)

(73) Assignee: Matrix Laboratories Limited, Secunderabad (IN)

( * ) Notice: Subject to any disclaimer, the term of this patent is extended or adjusted under 35 U.S.C. 154(b) by 200 days.

(21) Appl. No.: 13/121,387

(22) PCT Filed: Sep. 29, 2009

(86) PCT No.: PCT/IN2009/000526
§ 371 (c)(1),
(2), (4) Date: Mar. 28, 2011

(87) PCT Pub. No.: WO2010/035283
PCT Pub. Date: Apr. 1, 2010

(65) Prior Publication Data
US 2011/0184182 A1    Jul. 28, 2011

(30) Foreign Application Priority Data

Sep. 26, 2008  (IN) .......................... 2366/CHE/2008
Jan. 1, 2009   (IN) .............................. 02/CHE/2009

(51) Int. Cl.
*C07D 401/12*    (2006.01)

(52) U.S. Cl.
USPC ....................................... 546/273.7

(58) Field of Classification Search
USPC ....................................... 546/273.7
See application file for complete search history.

(56) References Cited

FOREIGN PATENT DOCUMENTS

EP    0451585 A2    10/1991
JP    3072458 A     3/1991

*Primary Examiner* — Patricia L Morris
(74) *Attorney, Agent, or Firm* — Maschoff Brennan

(57) ABSTRACT

Disclosed herein are novel compounds which are useful as intermediates for producing substituted sulfoxide compounds and a process for producing the same. Further disclosed is a process for producing the substituted sulfoxide compounds used as pharmacologically active agents, employing the novel intermediates of the present invention.

34 Claims, No Drawings

COMPOUNDS FOR PRODUCING SUBSTITUTED SULFOXIDES, PROCESS FOR PRODUCING THE SAME AND USE THEREOF

FIELD OF THE INVENTION

The present invention relates to novel compounds, process for producing the same and use thereof in the large scale production of substituted sulfoxides, their enantiomers or pharmaceutically acceptable salts thereof.

BACKGROUND OF THE INVENTION

Substituted sulfoxide compounds or their enantiomers (viz., Omeprazole, Lansoprazole, Pantoprazole, Rabeprazole and Ilaprazole) are known inhibitors of gastric acid secretion and are used as anti-ulcer agents. The sulfur atom of the sulfoxide group in asymmetrically substituted sulfoxide is chiral. This type of chiral sulfoxides has been discussed in the scientific literature since the late seventies, even though there is no literature evidence for efficient asymmetric process for the synthesis of the single enantiomers thereof.

The single enantiomers of pharmacologically active compounds have met an increased interest in the last years because of improved pharmacokinetic and biological properties. Therefore, there is a demand for an enantioselective process that can be used in large scale manufacture of the single enantiomers of pharmacologically active compounds, such as for instance optically pure, substituted 2-(2-pyridinylmethylsulphinyl)-1H-benzimidazoles.

The resolution processes of racemates of substituted sulfoxides are disclosed in DE 4035455. According to the disclosed process racemic sulfoxide is converted to a diastereomeric mixture, followed by separation of diastereomers and isolation of desired isomer from the separated diastereomer.

The international patent application WO96/02535 describes a process for the enantioselective synthesis of proton pump inhibitors using chiral titanium complexes. The resolution processes disclosed in the above prior arts are lengthy and tedious. They involve multiple steps during synthesis and purification to obtain the desired products.

Hence, there is a need for an improved and effective enantioselective process for large scale production of substituted sulfoxide compounds.

SUMMARY OF THE INVENTION

It is an aspect of the present invention to provide novel compounds or enantiomers thereof which are useful to produce in large scale of substituted sulfoxides, their enantiomers or pharmaceutically acceptable salts thereof.

It is yet another aspect of the present invention to provide a process for producing the novel compounds useful in the production of substituted sulfoxides.

It is another aspect of the present invention to provide a process for commercial scale production of substituted sulfoxides, their enantiomers or pharmaceutically acceptable salts thereof.

In accordance with an embodiment of the present invention, there is provided novel compound of formula 9

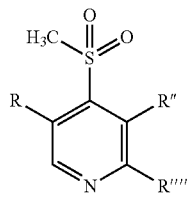

Formula-9 wherein
R represents hydrogen atom or alkyl group such as methyl;
R" represents an alkyl or alkoxy group such as methyl and methoxy;
R"" represents a group selected from methyl, chloromethyl, hydroxymethyl or a compound of formula 10 or 11, wherein when R"" is methyl, N is present as N-Oxide

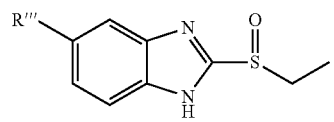

Formula -10

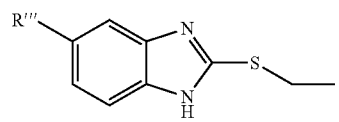

Formula-11

R''' represents a hydrogen atom or an alkoxy group optionally interrupted by one or more heteroatoms, or a heterocyclic group, the alkoxy group selected from methoxy and difluoromethoxy and the heterocyclic group selected from pyrrole.

In accordance with another embodiment of the present invention there is provided a process for producing substituted sulfoxides of formula I or 1a or enantiomer thereof wherein the process comprising reacting N-oxide of formula-1 with alkali salt of methylmercaptane to obtain thio derivative of formula-2 followed by oxidation using a suitable oxidizing agent to obtain a mesyl derivative of formula-3, chlorinating the mesyl derivative of formula-3 in a suitable solvent to obtain a compound of formula-5 or its salts, followed by condensing the compound of formula-5 with 2-mercaptobenzimidazole of compound of formula-8 in the presence of a suitable base to obtain a benzimidazole sulfide of formula-6, oxidizing the compound of formula-6 in a suitable solvent to obtain benzimidazole sulfoxide of formula-7a; stereoselectively oxidizing the compound of formula-6 using an optically active compound in the presence of a metal catalyst and a suitable solvent to obtain the compound of formula-7b and subsequently reacting the compound of formula-7a or 7b with an alcohol of formula HOR' to obtain substituted sulfoxides and their enantiomers or a pharmaceutically acceptable salt thereof.

In accordance with yet another embodiment of the present invention, there is provided a process for producing (R)-(+) 2-([3-methyl-4-(2,2,2-trifluoroethoxy)pyridin-2-yl]methylsulfinyl)-1H-benzimidazole comprising reacting 4-chloro-2, 3-dimethyl-pyridine-1-oxide with sodium methane thiolate to give 2,3-dimethyl-4-methylsulfanyl-pyridine-1-oxide followed by oxidation using a suitable oxidizing agent to obtain (4-methanesulfonyl-2,3-dimethyl-pyridine)-1-oxide, chlorinating the resultant in the presence of suitable chlorinating agent to obtain 2-chloromethyl-4-methanesulfonyl-3-methylpyridine, condensing the 2-chloromethyl-4-methanesulfonyl-3-methylpyridine in presence of a suitable base in a solvent, optionally in the presence of a phase transfer catalyst with 2-mercaptobenzimidazole to obtain 2-(4-methanesulfonyl-3-methyl-pyridine-2-ylmethylsulfonyl)-1-H-benzimidazole, stereoselective oxidation of the 2-(4-methanesulfonyl-3-methyl-pyridine-2-ylmethylsulfonyl)-1-H-benzimidazole using an optically active compound in presence of a metal catalyst and a suitable solvent to obtain (R)-2-(4-methanesulfonyl-3-methyl-pyridin-2-ylmethanesulfinyl)-1H-benzimidazole and subsequently reacting the (R)-2-(4-methanesulfonyl-3-methyl-pyridin-2-ylmethanesulfinyl)-1H-benzimidazole with trifluoroethanol to obtain the (R)-(+)2-([3-methyl-4-(2,2,2-trifluoroethoxy)pyridin-2-yl]methylsulfinyl)-1H-benzimidazole.

In accordance with a further embodiment of the present invention, there is provided a process for producing substituted sulfoxide compounds comprising reacting benzimidazole sulfoxide of Formula-7a or 7b with an alcohol of formula HOR' to obtain substituted sulfoxide compound of formula-I or formula-Ib in the presence of a suitable base.

DETAILED DESCRIPTION OF THE INVENTION

While this specification concludes with claims particularly pointing out and distinctly claiming that, which is regarded as the invention, it is anticipated that the invention can be more readily understood through reading the following detailed description of the invention and study of the included examples.

The present invention provides novel compounds which are useful intermediates for producing substituted sulfoxide compounds, their enantiomers or pharmaceutically acceptable salts thereof. In addition the present invention provides a process for producing the novel compounds of the invention and use thereof for producing substituted sulfoxide compounds, their enantiomers or pharmaceutically acceptable salts thereof.

The present invention further provides a novel process for producing substituted sulfoxides, their enantiomers and pharmaceutically acceptable salts thereof employing the novel intermediates of the invention.

Moreover, the present invention encompasses a process for producing (R)-(+)2-([3-methyl-4-(2,2,2-trifluoroethoxy)pyridin-2-yl]methylsulfinyl)-1H-benzimidazole (dexlansoprazole) employing the novel compounds of the invention as intermediates.

According to the present invention, the disclosed novel compounds provided herein at least one chemical entity chosen from compounds of formula 9

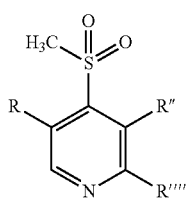

Formula-9 wherein

R represents hydrogen atom or alkyl group such as methyl;

R" represents an alkyl or alkoxy group such as methyl and methoxy;

R"" represents a group selected from methyl, chloromethyl, hydroxymethyl or a compound of formula 10 or 11, wherein when R"" is methyl, N is present as N-Oxide

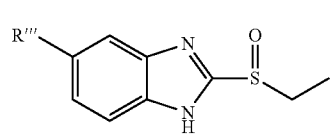

Formula-10

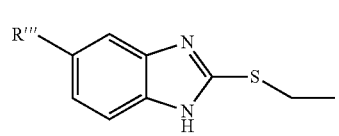

Formula-11

R'" represents a hydrogen atom or an alkoxy group optionally interrupted by one or more heteroatoms, or a heterocyclic group, the alkoxy group selected from methoxy and difluoromethoxy and the heterocyclic group selected from pyrrole.

Among the novel compounds of formula 9 disclosed herein, one is of formula 3 wherein R and R" are as defined above

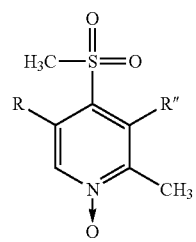

Formula-3

Another novel compound of formula 9 disclosed herein, is the compound of formula 4 wherein R and R" are as defined above.

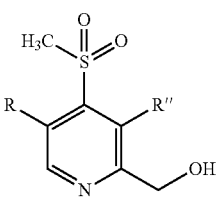

Formula-4

Still another novel compound of formula 9 disclosed herein, is the compound of formula 5 wherein R and R" are as defined above.

Formula-5

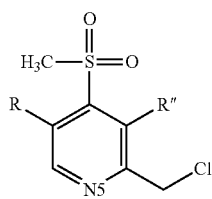

Another novel compound of formula 9 disclosed herein, is the compound of formula 6 or its enantiomer wherein R, R" and R''' are as defined above.

Formula-6

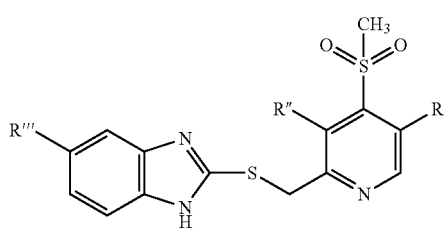

Further, another novel compound of formula 9 disclosed herein, is the compound of formula 7a or its enantiomer wherein R, R" and R''' are as defined above.

Formula-7a

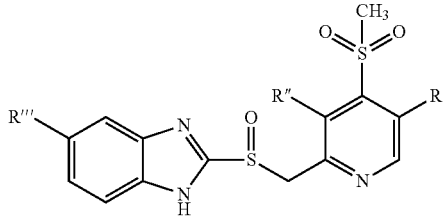

According to the present invention, the process for producing substituted sulfoxides of formula I or Ia and their enantiomers as illustrated by the following Scheme-I, wherein X represents halogen such as chlorine, bromide and the like and R, R', R" and R''' are as defined above and R' represents an alkyl group containing 1-6 carbon atoms, optionally interrupted by one or more oxygen atom(s) or haloalkyl group, the alkyl group is selected from methyl, ethyl, n-propyl, isopropyl, butyl and the optionally interrupted alkyl group is selected from 3-methoxypropyl group and the haloalkyl group is selected from trifluoroethyl, difluoromethyl.

Formula-I

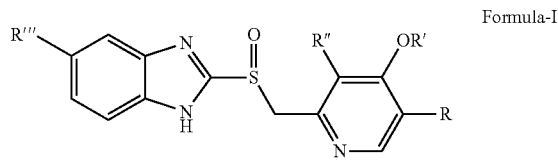

Formula-Ia

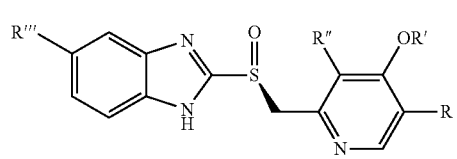

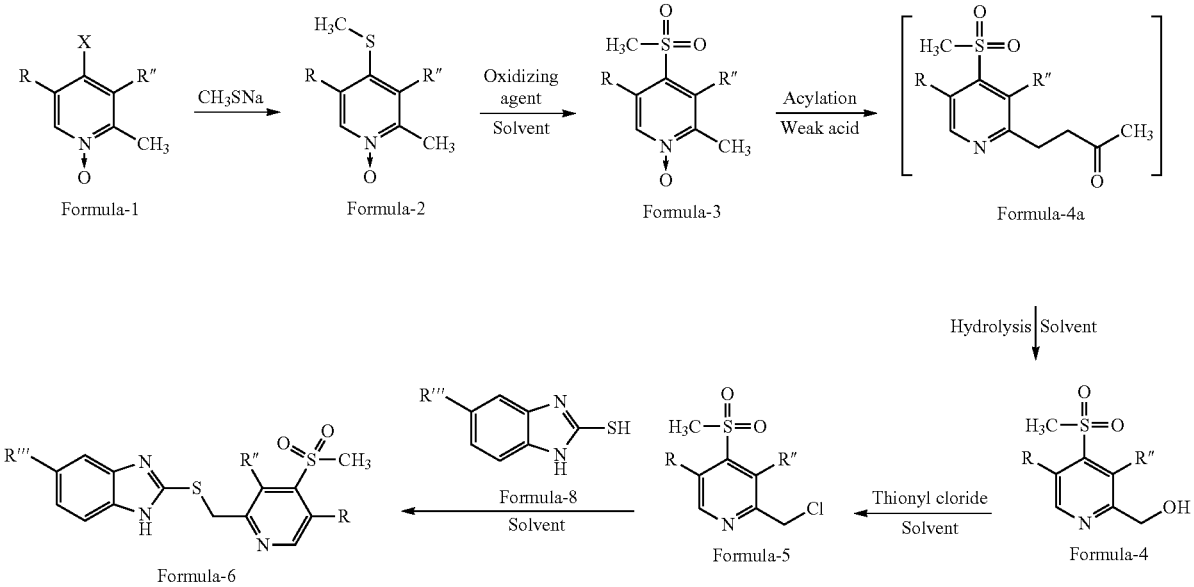

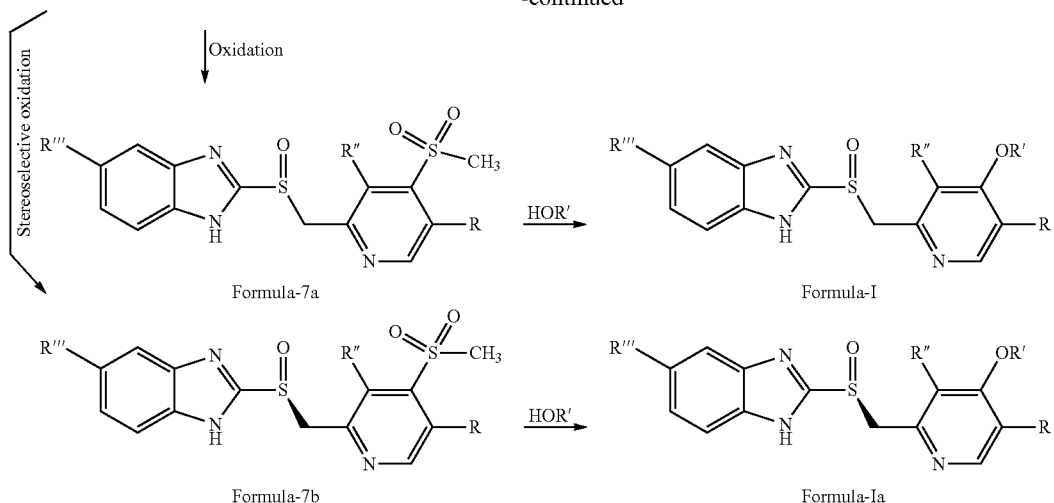

According to the present invention the process for producing substituted sulfoxides of the compound of formula-I or formula-Ia comprises the steps of:

a) reacting N-oxide of formula-1 with alkali salt of methylmercaptane to obtain thio derivative of formula-2 followed by oxidation using a suitable oxidizing agents to obtain the mesyl derivative of formula-3, b) acetylating compound of formula-3 followed by hydrolysis to obtain alcohol derivative compound of formula-4, c) chlorinating the alcohol derivative of formula-4 in a suitable solvent to obtain compound of formula-5, d) condensing the compound of formula-5 with 2-mercaptobenzimidazole of compound of formula-8 in the presence of a suitable base to obtain benzimidazole sulfide of the formula-6, e) oxidizing the benzimidazole sulfide of Formula-6 in a suitable solvent to obtain benzimidazole sulfoxide of Formula-7a, f) stereoselectively oxidizing the benzimidazole sulfide of formula-6 using an optically active compound in the presence of a metal catalyst and suitable solvent obtain the compound of formula-7b, g) reacting the compound of Formula-7a or 7b with an alcohol of formula HOR' to get substituted sulfoxide compound of formula-I or compound of formula-Ia.

Alternatively, according to the present invention the process for producing substituted sulfoxides of formula I or Ia and their enantiomers is as illustrated by the following Scheme-II,

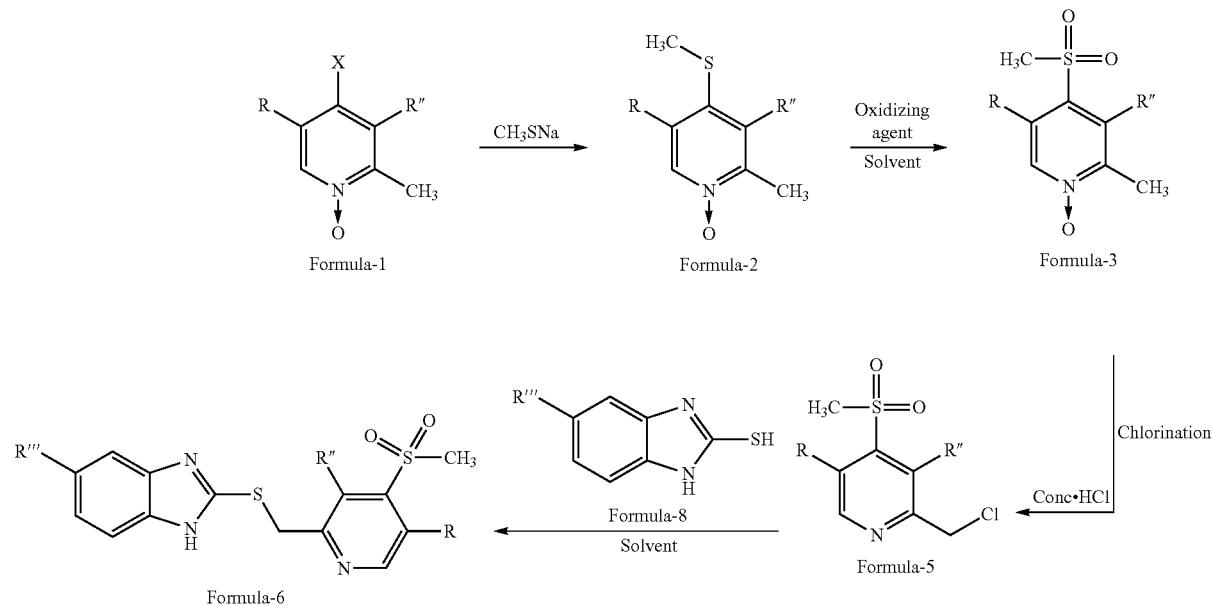

-continued

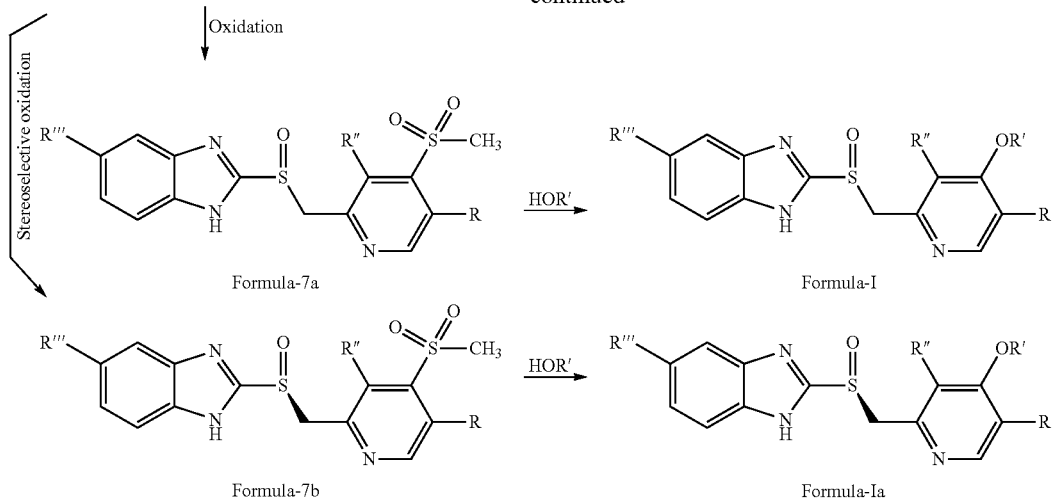

Further, in accordance with the present invention, the novel process for producing substituted sulfoxides of compound of formula-I or compound of formula-Ia comprises the steps of:
a) reacting N-oxide of formula-1 with alkali salt of methylmercaptane to obtain thio derivative of formula-2 followed by oxidation using a suitable oxidizing agents to obtain the mesyl derivative of formula-3,
b) chlorinating the mesyl derivative of formula-3 in a suitable solvent to obtain compound of formula-5 or its salts,
c) condensing compound of formula-5 with 2-mercaptobenzimidazole of compound of formula-8 in the presence of a suitable base to obtain benzimidazole sulfide of formula-6,
d) oxidizing benzimidazole of formula-6 in a suitable solvent to obtain benzimidazole sulfoxide of formula-7a,
e) stereoselectively oxidizing the benzimidazole sulfide of formula-6 using an optically active compound in the presence of a metal catalyst and suitable solvent obtain the compound of formula-7b,
f) reacting benzimidazole sulfoxide of formula-7a or 7b with an alcohol of formula, HOR to get substituted sulfoxide compound of formula-I or formula-Ia.

According to the present invention the process for producing dexlansoprazole is as illustrated by the following Scheme-III

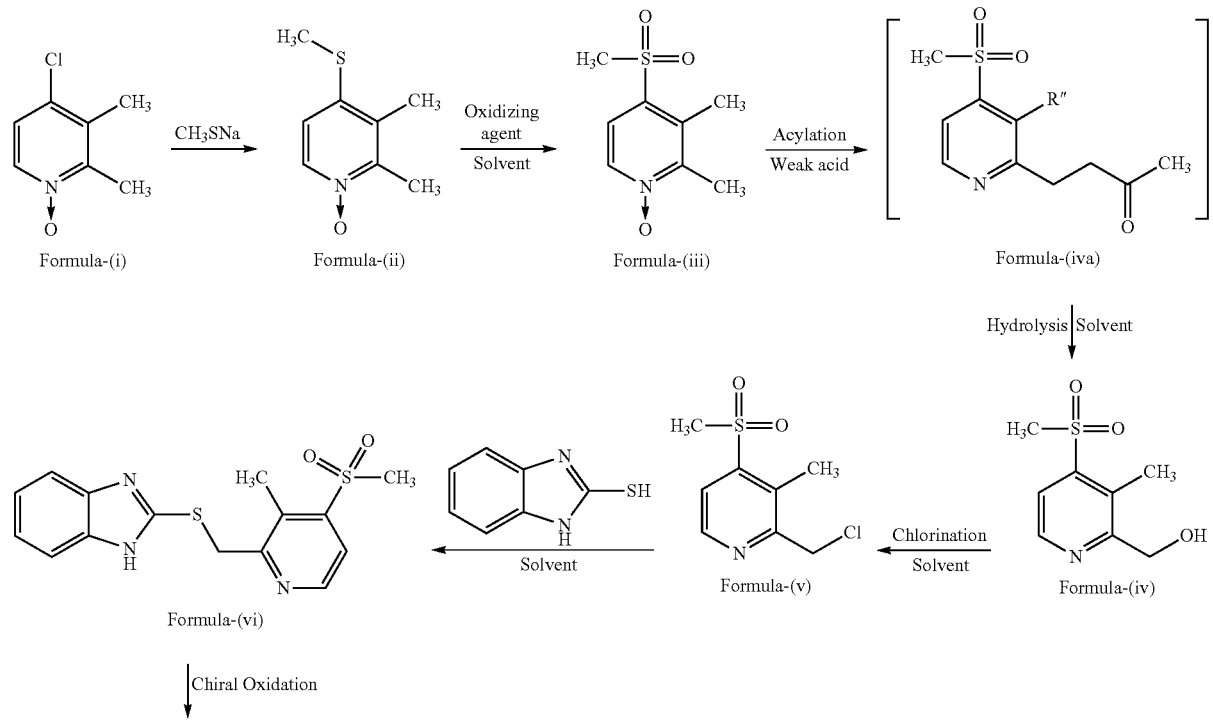

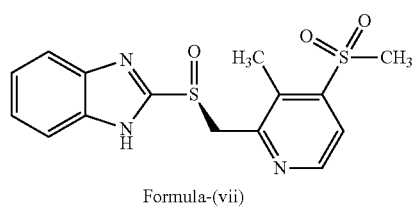

Formula-(vii)

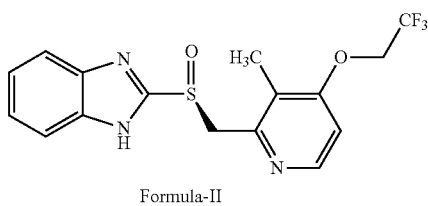

Formula-II

In accordance with the present invention the process for producing dexlansoprazole, comprises the steps of:
a) reacting 4-chloro-2,3-dimethyl-pyridine-1-oxide of Formula-(i) with sodium methane thiolate to give 2,3-dimethyl-4-methylsulfanyl-pyridine 1-oxide Formula-(ii) followed by oxidation using suitable oxidizing agent to obtain (4-methanesulfonyl-2,3-dimethyl-pyridine)1-oxide compound of Formula-(iii),
b) acetylating the (4-methanesulfonyl-2,3-dimethyl-pyridine)-1-oxide compound of Formula-(iii) followed by hydrolysis to obtain alcohol derivative of (4-methanesulfonyl-3-methyl-pyridin-2-yl)-methanol compound of Formula-(iv),
c) chlorinating the (4-methanesulfonyl-3-methyl-pyridin-2-yl)-methanol compound of Formula-(iv), in the presence of suitable chlorinating agent to obtain 2-chloromethyl-4-methanesulfonyl-3-methylpyridine of compound of Formula-(v),
d) condensing the compound of Formula-(v) with 2-mercaptobenzimidazole to obtain 2-(4-methanesulfonyl-3-methyl-pyridine-2-ylmethylsulfonyl)-1-H-benzimidazole of Formula-(vi) in the presence of a suitable base and suitable solvent,
e) stereoselectively oxidizing the benzimidazole sulphide of formula-(vi) using an optically active compound in presence of a metal catalyst and a suitable solvent to obtain (R)-2-(4-methanesulfonyl-3-methyl-pyridin-2-ylmethanesulfinyl)-1H-benzimidazole compound of Formula-(vii), and
f) reacting benzimidazole sulfoxide of Formula-(vii) with trifluoroethanol to get dexlansoprazole of Formula-II.

Alternatively, according to the present invention the process for producing dexlansoprazole is as illustrated by the following Scheme-IV Scheme-IV

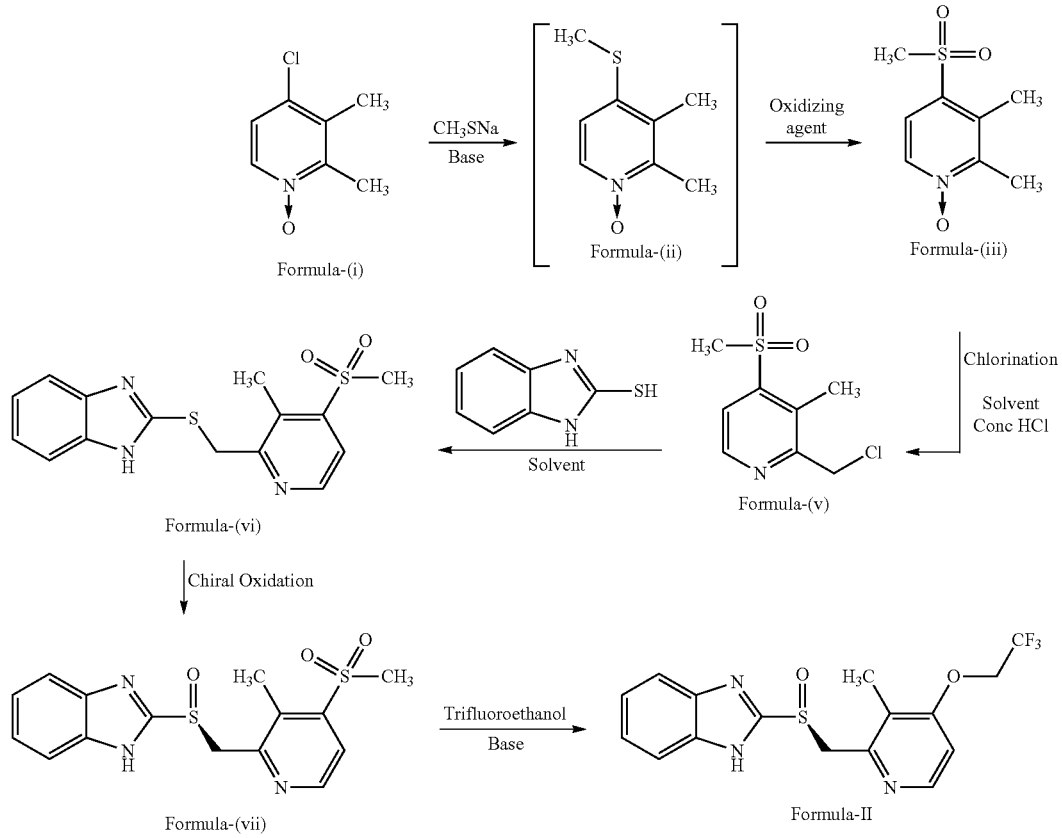

In accordance with the present invention the process for producing dexlansoprazole, comprises the steps of
a) reacting the 4-chloro-2,3-dimethyl-pyridine-1-oxide of Formula-(i) with sodium methane thiolate to obtain 2,3-dimethyl-4-methylsulfanyl-pyridine 1-oxide of formula-(ii) followed by oxidation to obtain thio derivative (4-methanesulfonyl-2,3-dimethyl-pyridine) 1-oxide compound of formula-(iii) using suitable a oxidizing agent in the presence of a catalyst,
b) chlorinating the (4-methanesulfonyl-2,3-dimethyl-pyridine) 1-oxide of formula-(iii) in the presence of suitable chlorinating agent to obtain the 2-chloromethyl-4-methanesulfonyl-3-methylpyridine of compound of formula-(v) or its salts,
c) condensing the compound of formula-(v) with 2-mercaptobenzimidazole to obtain the 2-(4-methanesulfonyl-3-methyl-pyridine-2-ylmethylsulfonyl)-1-H-benzimidazole of formula-(vi) in the presence of a suitable base and a solvent,
d) stereoselectively oxidizing the benzimidazole sulphide of formula-(vi) using an optically active compound in presence of a metal catalyst and a suitable solvent to obtain the (R)-2-(4-methanesulfonyl-3-methyl-pyridin-2-ylmethanesulfinyl)-1H-benzimidazole compound of formula-(vii),
e) reacting the benzimidazole sulfoxide of formula-(vii) with trifluoroethanol to obtain dexlansoprazole of Formula-II.

According to the present invention formation of thio derivative in step a) is optionally carried out in the presence of a phase transfer catalyst selected from tetrabutyl ammonium bromide, tetra ethyl ammonium bromide, tetra butyl ammonium acetate, tetra butyl ammonium fluoride, benzyl trimethyl ammonium chloride and the like.

The oxidizing agents used in step a) is selected from but not limited to metachloro peroxybenzoic acid, hydrogen peroxide, cumene hydroperoxide, sodium hypohalite. The solvents used in the oxidizing step a) include water, chlorinated aromatic or aliphatic hydrocarbons such as chloroform, methylene dichloride and the like.

The acetylating agent used in the present invention is acetic anhydride, acetyl chloride in presence of acetic acid at reflux temperature. The acetyl derivative is formed in situ. The hydrolysis is carried out in the presence of alkali or alkaline metal hydroxides such as lithium hydroxide, sodium hydroxide, potassium hydroxide, magnesium hydroxide or calcium hydroxide more preferably lithium hydroxide. The solvent is selected from alcohols such as methanol, ethanol, isopropanol, ketones such as acetone, methylethylketone or ethers such as tetrahydrofuran.

The chlorinating reagents used in the present invention include but not limited to thionylchloride, paratoluenesulfonyl chloride, alkane sulfonyl chloride such as methane sulfonyl chloride or ethane sulfonyl chloride, $POCl_3$, $PCl_5$, oxalyl chloride and the like. The solvents used in the chlorinating step include but not limited to chloroform, dichloroethane, carbon tetrachloride, benzene or toluene and the like.

The solvents used during the condensation process of the present invention are selected from water, alcohols such as methanol, ethanol, isopropanol and the like, ketones such as acetone, methylethylketone, methylisobutylketone and the like, nitriles such as acetonitrile or mixtures thereof.

The base used during the condensation process of the invention is selected from inorganic bases such as sodium hydroxide, sodium carbonate, sodium bicarbonate, sodium methoxide, potassium hydroxide, potassium carbonate, cesium carbonate, potassium bicarbonate, potassium tertiary-butoxide and the like. The condensation reaction is optionally carried out in the presence of a phase transfer catalyst.

The oxidizing agent used for the oxidation of compound of formula-6 in scheme-I & II is selected from metachloroperoxy benzoic acid, cumene hydrogen peroxide, hydrogen peroxide, sodium hypohalite and the like. The solvent used in the present step includes but not limited to water, hydrocarbons such as toluene, tetrahydrofuran, dioxane, diethylether, diisopropylether, chloroform, dichloromethane or dichloroethane and the like, alcohols such as methanol, ethanol, isopropanol and the like, ketones such as acetone, methylethylketone, methylisobutylketone and the like, esters such as ethylacetate and the like or nitriles such as acetonitrile and the like mixtures thereof. The oxidation is carried out optionally in the presence of base selected from triethylamine, diisopropylamine, diisopropylethylamine, dicyclohexylamine, cyclohexylamine, tri n-butylamine or diisopropyl ethylamine and the like.

According to the invention, chiral oxidizing agents are used for stereoselective oxidation of compound of formula-6 in schemes-I-IV, wherein the chiral oxidizing agent is selected from cumene hydrogen peroxide, metachloroperoxy benzoic acid, tert-butyl hydroperoxide, benzoyl peroxide, sulpholane and the like. The solvents used in the process step are selected from water, hydrocarbons such as toluene, chloroform, dichloromethane or dichloroethane and the like, ethers such as tetrahydrofuran, ketones such as acetone, methylethylketone, methylisobutylketone and the like, esters such as ethylacetate and the like or nitriles such as acetonitrile and the like or mixtures thereof. The base used in the present step includes but not limited to triethylamine, diisopropylamine, N,N-diisopropylethylamine, dicyclohexylamine, cyclohexylamine, tri-butylamine, n-butylamine or diisopropyl ethylamine, preferably N,N-diisopropylethylamine and the like.

The optically active reagent used in the present invention is selected from but not limited to enantiomerically pure mandelic acid, tartaric acid, diethyl tartaric acid, phenylethylamine, cinchonine, cinchonidine or brucine and the like. The metal catalyst is selected from barium acetate, strontium acetate, titanium, vanadium, molybdenum or zirconium, preferably Ti(IV) isopropoxide and the like.

The suitable base used in the replacement of mesyl group (substitution) in step (f) using the alcohol of the formula HOR' is selected from trifluoroethanol, 3-methoxypropanol or methanol is selected from but not limited to sodium hydroxide, potassium hydroxide, sodium hydride, calcium hydroxide, barium hydroxide, magnesium hydroxide, sodium carbonate, potassium carbonate, cesium carbonate, sodium methoxide, sodium tertiary butoxide, potassium tertiary butoxide and the like. The solvent used in the present step is selected from dimethylsulfoxide, dimethylformamide, dimethyl acetate, N-methylpyrrolidone, alcohols such as methanol, ethanol and the like, dioxane, toluene, xylene, tetrahydrofuran, dichloromethane or acetonitrile, sulpholane and the like or mixtures thereof.

According to another embodiment of the present invention a process for purifying (R)-2-(4-methanesulfonyl-3-methyl-pyridin-2-ylmethanesulfinyl)-1H-benzimidazole compound of Formula-(vii) comprising:
a) dissolving the (R)-2-(4-methanesulfonyl-3-methyl-pyridin-2-ylmethanesulfinyl)-1H-benzimidazole in a suitable solvent,
b) optionally adding an anti-solvent; and
c) isolating pure (R)-2-(4-methanesulfonyl-3-methyl-pyridin-2-ylmethanesulfinyl)-1H-benzimidazole.

The solvent used for purification the (R)-2-(4-methanesulfonyl-3-methyl-pyridin-2-ylmethanesulfinyl)-1H-benzimidazole is selected from water, ketones such as acetone, methylethylketone, methylisobutylketone, nitriles such as acetonitrile, alcohols such as methanol, ethanol, isopropanol or mixtures thereof and the antisolvent is selected from water.

Further, alternatively according to the present invention, there is provided a process for producing the substituted sulfoxide compound of formula-I or formula-Ia from the compound of formula-7a or 7b wherein the process comprises reacting benzimidazole sulfoxide of Formula-7a or 7b with the alcohol of formula HOR' in the presence of a suitable base to obtain the substituted sulfoxide compound of formula-I or formula-Ib.

In accordance with the process of the present invention the sulfone and sulphide impurities are minimized. Further the process of the present invention is cost effective and industrially feasible for large scale production. In addition, the process utilizes commercially available raw materials during the process, thereby making the process economical.

The following non-limiting examples illustrate specific embodiments of the present invention. They should not construe it as limiting the scope of present invention in any way.

Example-1

4-Methanesulfonyl-2,3-dimethyl-pyridine 1-oxide [Formula-(iii)]

Mixture of 4-chloro-2,3-dimethyl-pyridine-1-oxide (300 g), sodium methane ethiolate (20%) (900 ml) and tetra butyl ammonium bromide (30 g) were heated to 55-60° C. and maintained at the same temperature for about 1 to 2 hours and the reaction mixture is cooled to room temperature. Sodium tungsten dihydrate (15.75 g) was added to the reaction mixture and cooled to 0 to 10° C. Subsequently, 30% Hydrogen peroxide (866 ml) was added slowly to the reaction mixture at 20-30° C. and maintained at the same temperature for 3-4 hrs followed by maintenance at 0-10° C. for 1-2 hrs. The compound was filtered, washed with DM water (200 ml) and dried the wet compound at 50-60° C. to obtain 320 g of the title compound characterized by $^1$HNMR data (300 MHz): δ 2.30 (s, 3H), 2.5 (s, 3H), 2.55 (s, 3H), 6.87 (d, 1H), 8.16 (d, 1H) and mass $[M]^+$: 170.0.

Example-2

(4-Methanesulfonyl-2,3-dimethyl-pyridine)-1-oxide [Formula-(iii)]

Mixture of 2,3-dimethyl-4-methylsulfanyl-pyridine-1-oxide (40 g) and chloroform (200 ml) was cooled to 0-10° C. and mCPBA (122.5 g) was added slowly. The temperature of the reaction mixture was raised to 25-30° C. followed by quenching the reaction mixture with 30% sodium thiosulfate and separating the layers with chloroform (2×120 ml). All the organic layers were combined, washed with 5% NaOH solution and finally washed with 10% sodium chloride solution. Subsequently, the organic layer was dried over sodium sulphate and the solvent distilled off completely under vacuum. Ethylacetate (80 ml) was added to the reaction mixture, cooled to 0-10° C. and maintained at the same temperature for about 1 hour. The resultant compound was then filtered, washed with ethylacetate (10 ml) and dried the wet compound at 50° C. to get 25 g of the title compound characterized by $^1$HNMR data (300 MHz): δ 2.56 (s, 3H), 2.70 (s, 3H), 3.13 (s, 3H), 7.80 (d, 1H), 8.26 (d, 1H) and mass $[M]^+$: 202.06.

Example-3

(4-Methanesulfonyl-3-methyl-pyridin-2-yl)-methanol [Formula-(iv)]

To a mixture of (4-Methanesulfonyl-2,3-dimethyl-pyridine)-1-oxide (24 g) and acetic acid (50 ml) was added acetic anhydride (28.2 ml), followed by heating to reflux and maintaining the same temperature for about 3 hrs. The reaction mass was cooled to 80° C. and methanol (25 ml) was added followed distilling off the solvent completely under vacuum. THF:methanol (125:25 ml), LiOH (7.5 g) was added to the crude at 25-30° C. followed by adding DCM (100 ml) to the reaction mixture and extraction with (2×150 ml) DCM. All the organic layers were combined and washed with saturated sodium chloride solution (25 ml). The organic layer was dried over sodium sulphate and distilled off completely under vacuum. Subsequently, n-hexane (100 ml) was added to the reaction mass, the compound filtered and washed with n-hexane (10 ml). The wet compound was then dried at 50-55° C. to yield 14 g of the title compound characterized by $^1$HNMR data (300 MHz): δ 2.58 (s, 3H), 3.13 (s, 3H), 4.62 (s, 1H), 4.80 (s, 2H), 7.86 (d, 1H), 8.68 (d, 1H) and mass $[M]^+$: 202.06.

Example-4

2-chloromethyl-4-methanesulfonyl-3-methylpyridine [Formula-(v)]

To a mixture of (4-Methanesulfonyl-3-methyl-pyridin-2-yl)-methanol (13 g) and chloroform (130 ml) was added thionylchloride (7.5 ml) at 25-30° C. The reaction mixture was then heated to 60-65° C. and maintained at the same temperature for about 30 min. The solvent was distilled off completely under vacuum at 50-55° C. Ethylacetate (52 ml) was added to the crude followed by cooling to 0-10° C. and maintaining the same temperature for about 2 hrs. The compound is then filtered and washed the solid with ethylacetate (10 ml). The compound at 50-55° C. to obtain 12.2 gm of the title compound characterized by $^1$HNMR data (300 MHz): δ 2.75 (s, 3H), 3.38 (s, 3H), 4.95 (s, 2H), 7.82 (d, 1H), 8.70 (d, 1H) and mass $[M]^+$: 220.06.

Example-5

2-chloromethyl-4-methanesulfonyl-3-methylpyridine hydrochloride salt

Mixture of 4-Methanesulfonyl-2,3-dimethyl-pyridine 1-oxide (100 g) and methane sulfonyl chloride (300 ml) was heated to 90-95° C. and maintained at the same temperature for 3-4 hrs. 20% sodium hydroxide solution (1500 ml) was cooled to 0-5° C. separately and the above reaction mixture was added to this solution slowly for a period of 2-3 hrs and maintained at the same temperature for 1-2 hrs. The solid was filtered and washed with DM water (200 ml). DM water (400 ml) was added to the wet material and stirred for 30-60 min at 25-35° C. The solid was filtered and washed with DM water (100 ml). Ethylacetate (600 ml) was added to the wet material followed by heating to get clear solution and adding carbon (10 gm) and stirring the reaction mixture for 30 minutes. The resultant reaction mass was filtered through hiflow bed and washed with ethyl acetate (200 ml). The filtrate was dried with sodium sulfate (100 gm). Subsequently, conc. HCl (60 ml) was added, heated to reflux and maintained at the same temperature for 30-60 min. The reaction mixture was cooled to 25-30° C., then to 0-5° C. and maintained at the same temperature for 1-2 hrs. The solid was then filtered and washed with ethylacetate (100 ml). The wet compound was dried at 50-60° C. 90 g of the title compound was obtained.

Example-6

2-(4-methanesulfonyl-3-methyl-pyridine-2-ylmethyl-sulfonyl)-1-H-benzimidazole [Formula-(vi)]

To a mixture of 10% aq. acetone (397 ml acetone+44 ml DM water) and 2-chloromethyl-4-methanesulfonyl-3-methylpyridine hydrochloride (49 g) was added 2-mercaptobenzimidazole (28.65 g), potassium carbonate (42.17 gm) followed by heating to reflux temperature and maintaining at the same temperature for about 1-2 hrs. The solvent was distilled off completely under vacuum. To the crude thus obtained DM water (490 ml) was added followed by stirring, filtering and washing the solid with DM water (50 ml). To the wet compound 5% sodium hydroxide solution (245 ml) was added, followed by stirring, filtering and washing with DM water (150 ml). The wet compound was dried at 50-60° C. to obtain 59 gm of the title compound.

Example-7

(R)-2-(4-Methanesulfonyl-3-methyl-pyridin-2-ylmethanesulfinyl)-1H-benzimidazole [Formula-(vii)]

To a mixture of 2-(4-methanesulfonyl-3-methyl-pyridineylmethylsulfonyl)-1-H-benzimidazole (25 g), tetrahydrofuran (625 ml) and water (0.08 gm) was added (+)-diethyl-L-tartrate (31 gm) under nitrogen atmosphere and heated to 50 to 60° C. Subsequently, Ti(IV)isopropoxide (21.3 gm) was added to the reaction mixture at 50 to 60° C. and maintained at the same temperature for about 45-60 min. The reaction mixture was cooled to 20-25° C. and diisopropylethylamine (9.7 g) was added and maintained at the same temperature for 10-15 min. Cumene hydroperoxide (80% 15 ml) was then added to the reaction mixture and maintained at the same temperature for 2 hours. To the reaction mixture was added 10-12% aq. ammonia solution (100 ml) and maintained for 15 min. The layers were separated and 10-12% aq. ammonia solution (100 ml) was added to the organic layer at 20-25° C., maintained for 15 min and the steps repeated for two or three times. Combined all the aq. ammonia solution layers and cooled to 0-10° C. Adjusted the pH of the reaction mixture to 7.0 to 7.5 with acetic acid (125 ml) at 0 to 10° C. Distilled off the tetrahydrofuran traces at 40° C. under reduced pressure. Cooled the reaction mixture to 0 to 10° C. and maintained at the same temperature for about one to two hours. Filtered the solid and washed with DM water (50 ml) and dried to give 18 g of the title compound.

Example-8

Purification of (R)-2-(4-Methanesulfonyl-3-methyl-pyridin-2-ylmethanesulfinyl)-1H-benzimidazole [Formula-(vii)]

To a mixture of acetone (800 ml), acetonitrile (100 ml) and methanol (100 ml) was added (R)-2-(4-Methanesulfonyl-3-methyl-pyridin-2-ylmethanesulfinyl)-1H-benzimidazole obtained in Ex-7 at 25-30° C., the reaction mass heated to reflux temperature and maintained at the reflux temperature for about 30-60 min. The reaction mass was cooled to 20-25° C. and stirred for about 1-2 hrs. The resultant compound was filtered and washed with acetone (50 ml). The wet compound was then dried in air oven at 45-50° C. for about 6-8 hrs to yield 76 gm of the title compound.

Chiral Purity—99.99% (ee); Purity by HPLC—99.90%; Sulfone: 0.10%.

Example-9

Purification of (R)-2-(4-Methanesulfonyl-3-methyl-pyridin-2-ylmethanesulfinyl)-1H-benzimidazole [Formula-(vii)]

To a mixture of acetone (80 ml), acetonitrile (10 ml) and methanol (10 ml) was added (R)-2-(4-Methanesulfonyl-3-methyl-pyridin-2-ylmethanesulfinyl)-1H-benzimidazole obtained in Ex-7 at 25-30° C., the reaction mass heated to reflux temperature and maintained at the reflux temperature for about 30-60 min. DM water (10 ml) was added slowly to the reaction mass at reflux temperature to get clear solution and the reflux temperature maintained for about 30-60 min. The reaction mass was cooled to 10-15° C. and stirred for about 1-2 hrs. The compound was filtered and washed with acetone (10 ml). The wet compound was then dried in air oven at 45-50° C. for about 6-8 hrs to yield 76 gm of the title compound.

/Chiral Purity—99.97% (ee); Purity by HPLC—99.98%; Sulfone: 0.02%.

Example-10

Purification of (R)-2-(4-methanesulfonyl-3-methyl-pyridin-2-ylmethanesulfinyl)-1H-benzimidazole [Formula-(vii)]

To a mixture of acetone (40 ml) and acetonitrile (10 ml) was added (R)-2-(4-Methanesulfonyl-3-methyl-pyridin-2-ylmethanesulfinyl)-1H-benzimidazole obtained in Ex-7 at 25-30° C., the reaction mass heated to reflux temperature and maintained at the reflux temperature for about 30-60 min. The reaction mass was then cooled to 25-30° C. and stirred for about 1-2 hrs. The compound was filtered and washed with acetone (10 ml). The wet compound was dried in air oven at 45-50° C. for about 6-8 hrs to yield 3.8 gm of the title compound.

Chiral Purity—99.63% (ee); Purity by HPLC—99.53%; Sulfone: 0.44%.

Example-11

Purification of (R)-2-(4-methanesulfonyl-3-methyl-pyridin-2-ylmethanesulfinyl)-1H-benzimidazole [Formula-(vii)]

To a mixture of acetone (30 ml) and DM water (10 ml) was added (R)-2-(4-Methanesulfonyl-3-methyl-pyridin-2-ylmethanesulfinyl)-1H-benzimidazole obtained in Ex-7 at 25-30° C., the reaction mass heated to reflux temperature and maintained at the reflux temperature for about 30-60 min. The reaction mass was cooled to 25-30° C. and stirred for about 1-2 hrs. The compound was filtered and washed with acetone (10 ml). The wet compound was then dried in air oven at 45-50° C. for about 6-8 hrs to yield 2.5 gm of the title compound.

Chiral Purity—99.85% (ee); Purity by HPLC—99.84%; Sulfone: 0.12%.

Example-12

Purification of (R)-2-(4-methanesulfonyl-3-methyl-pyridin-2-ylmethanesulfinyl)-1H-benzimidazole [Formula-(vii)]

To a mixture of acetone (30 ml), DM water (10 ml) and acetonitrile (10 ml) was added (R)-2-(4-Methanesulfonyl-3-methyl-pyridin-2-ylmethanesulfinyl)-1H-benzimidazole obtained in Ex-7 at 25-30° C., the reaction mass heated to reflux temperature and maintained at the reflux temperature for about 30-60 min. The reaction mass was cooled to 25-30° C. and stirred for about 1-2 hrs. The compound was filtered and washed with acetone (10 ml) and the wet compound dried in air oven at 45-50° C. for about 6-8 hrs to yield 4.5 gm of the title compound.
Chiral Purity—99.99% (ee); Purity by HPLC—99.91%; Sulfone: 0.04%.

Example-13

Production of (R)-2-[3-Methyl-4-(2,2,2-trifluoro-ethoxy)-pyridin-2-ylmethane sulfinyl]-1H-benzimidazole [Formula-(II)]

To a mixture of dimethyl formamide (200 ml) and potassium tertiary butoxide (32.0 g) was added trifluoroethanol (28.65 g) slowly at 25-30° C. and stirred for about 30 minutes. (R)-2-(4-methanesulfonyl-3-methyl-pyridine-2-ylmethyl-sulfonyl)-1-H-benzimidazole (20 g) was added to the reaction mixture and maintained at the same temperature for about 24 hours. The reaction mixture was cooled to 0-10° C. and DM water (800 ml) was added at the same temperature. The pH of the reaction mixture was adjusted to 7.0 to 7.5 with acetic acid at 0-10° C. and maintained at the same temperature for about 1-2 hours. The compound was filtered and washed with DM water (30 ml) and the compound dried at 50-60° C. to obtain 19.3 g of the title compound.

Certain modifications and improvements of the disclosed invention will occur to those skilled in the art without departing from the scope of invention, which is limited only by the appended claims.

We claim:

1. A process for producing a substituted sulfoxide compound of formula-I or formula-Ia enantiomer thereof,

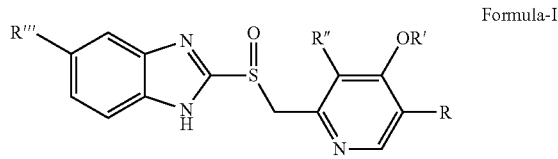

Formula-I

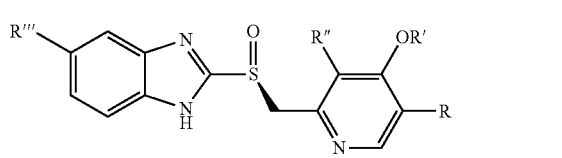

Formula-Ia in which,

R represents hydrogen atom or lower alkyl group;

R' represents an alkyl group containing 1-6 carbon atoms, optionally interrupted by one or more oxygen atom(s) or haloalkyl, the alkyl group is selected from methyl, ethyl, n-propyl, isopropyl, or butyl and the optionally interrupted alkyl group is selected from 3-methoxypropyl group and the haloalkyl group is selected from trifluoroethyl or difluoromethyl;

R" represents an alkyl group selected from methyl, ethyl or propyl or an alkoxy group;

R''' represents a hydrogen atom or an alkoxy group optionally interrupted by one or more heteroatoms, or a heterocyclic group, the alkoxy group selected from methoxy and difluoromethoxy and the heterocyclic group selected from pyrrole;

wherein the process comprising:

a) reacting N-oxide of formula-1

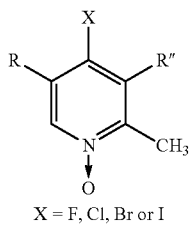

Formula-1

X = F, Cl, Br or I with alkali salt of methylmercaptane to obtain thio derivative of formula-2 followed by

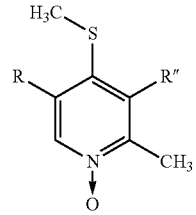

Formula-2 oxidation using an oxidizing agent to obtain a mesyl derivative of formula-3;

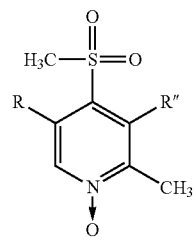

Formula-3 b) chlorinating the mesyl derivative of formula-3 in a solvent to obtain a compound of formula-5 or its salt;

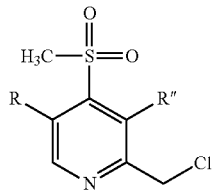

Formula-5 c) condensing the compound of formula-5 with 2-mercaptobenzimidazole of compound of formula-8 in the presence of a base to obtain a benzimidazole sulfide of formula-6.

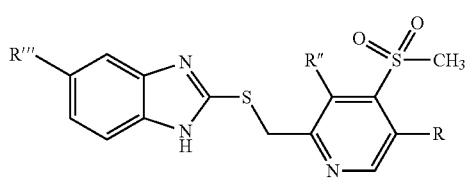

Formula-6 d) oxidizing the compound of formula-6 in a solvent to obtain benzimidazole sulfoxide of formula-7a;

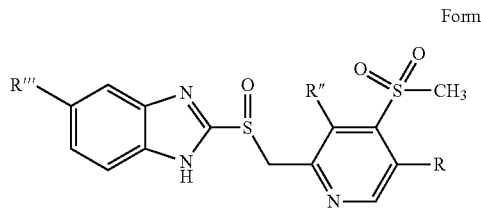

Formula-7a e) stereoselectively oxidizing the compound of formula-6 using an optically active compound in the presence of a metal catalyst and a solvent to obtain the compound of formula-7b; and

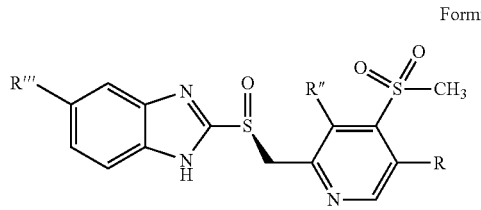

Formula-7b f) reacting the compound of formula-7a or 7b with an alcohol of formula HOR' to obtain substituted sulfoxide compound of the formula-I or the formula-Ib respectively.

2. A process for producing (R)-(+)-2-([3-methyl-4-(2,2,2-trifluoroethoxy)pyridin-2-yl]methylsulfinyl)-1H-benzimidazole, the process comprising, a) reacting 4-chloro-2,3-dimethyl-pyridine-1-oxide with sodium methane thiolate to give 2,3-dimethyl-4-methylsulfanyl-pyridine-1-oxide followed by oxidation using an oxidizing agent to obtain (4-methanesulfonyl-2,3-dimethyl-pyridine)-1-oxide;

b) chlorinating the (4-methanesulfonyl-2,3-dimethyl-pyridine) 1-oxide in the presence of a chlorinating agent to obtain 2-chloromethyl-4-methanesulfonyl-3-methylpyridine;

c) condensing the 2-chloromethyl-4-methanesulfonyl-3-methylpyridine in presence of a base in a solvent, optionally in the presence of a phase transfer catalyst with 2-mercaptobenzimidazole to obtain 2-(4-methanesulfonyl-3-methylpyridine-2-ylmethylsulfonyl)-1-H-benzimidazole;

d) stereoselective oxidation of the 2-(4-methanesulfonyl-3-methyl-pyridine-2-ylmethylsulfonyl)-1-H-benzimidazole using an optically active compound in presence of a metal catalyst and a solvent to obtain (R)-2-(4-methanesulfonyl-3-methylpyridin-2-ylmethanesulfinyl)-1H-benzimidazole; and e) reacting the (R)-2-(4-methanesulfonyl-3-methyl-pyridin-2-ylmethanesulfinyl)-1H-benzimidazole with trifluoroethanol to obtain the (R)-(+)-2-([3-methyl-4-(2,2,2-trifluoroethoxy)pyridin-2-yl]methylsulfinyl)-1H-benzimidazole.

3. The process according to claim 1, wherein the oxidizing agent used in step a) is selected from a group consisting of metachloroperbenzoic acid, hydrogen peroxide, cumene hydroperoxide or sodium hypohalite.

4. The process according to claim 1, wherein the solvent used in step a) is selected from water, chlorinated aromatic or aliphatic hydrocarbons.

5. The process according to claim 1, wherein the chlorinating agent used in step b) is selected from thionylchloride, paratoluenesulfonyl chloride, methane sulfonyl chloride or ethane sulfonyl chloride, POCl$_3$, PCl$_5$ or oxalyl chloride.

6. The process according to claim 1, wherein the solvent used in step b) is selected from chloroform, dichloroethane, carbontetrachloride, benzene or toluene.

7. The process according to claim 1, wherein the base used in step c) is selected from sodium hydroxide, potassium hydroxide, barium hydroxide, sodium carbonate, potassium carbonate, cesium carbonate, sodium bicarbonate or potassium bicarbonate.

8. The process according to claim 1, wherein the oxidizing agent used in step d) is selected from metachloroperbenzoic acid, cumene hydrogen peroxide, hydrogen peroxide or sodium hypohalite.

9. The process according to claim 1, wherein the stereoselective oxidation is carried out in the presence of an oxidizing agent selected from cumene hydrogen peroxide, metachloroperbenzoicacid, tert-butyl hydroperoxide, benzoyl peroxide, or sodium hypohalite.

10. The process according to claim 1, wherein the solvent used for stereoselective oxidation is selected from water, hydrocarbons, ethers, ketones, esters, nitriles or mixtures thereof.

11. The process according to claim 1, wherein the solvent used for stereoselective oxidation is selected from water, toluene, chloroform, dichloromethane, dichloroethane, tetrahydrofuran, acetone, methylethylketone, methylisobutylketone, ethylacetate, acetonitrile or mixtures thereof.

12. The process according to claim 1, wherein the base used for stereoselective oxidation is selected from the group of triethylamine, diisopropylamine, N,N-diisopropylethylamine, dicyclohexylamine, cyclohexylamine, tri-butylamine, n-butylamine or diisopropyl ethylamine.

13. The process according to claim 1, wherein the optically active reagent used for stereoselective oxidation is selected from enantiomerically pure mandelic acid, tartaric acid, diethyl tartaric acid, phenylethylamine, cinchonine, cinchonidine or brucine.

14. The process according to claim 1, wherein the metal catalyst used for stereoselective oxidation is selected from barium acetate, strontium acetate, titanium, vanadium, molybdenum or zirconium.

15. The process according to claim 1, wherein the alcohol of the formula HOR' is selected from trifluoroethanol, 3-methoxypropanol or methanol.

16. The process according to claim 1, wherein the base used in the substitution of benzimidazole sulphoxide is selected from sodium hydroxide, potassium hydroxide, sodium hydride, calcium hydroxide, barium hydroxide, magnesium hydroxide, sodium carbonate, potassium carbonate, cesium carbonate, sodium methoxide, sodium tertiary butoxide or potassium tertiary butoxide.

17. The process according to claim 1, wherein the solvent used in the substitution of benzimidazole sulphoxide is selected from dimethylsulfoxide, dimethylformamide, dimethyl acetate, N-methylpyrrolidone, methanol, ethanol, dioxane, toluene, xylene, tetrahydrofuran, dichloromethane acetonitrile, sulpholane or mixtures thereof.

18. The process for producing dexlansoprazole of compound of Formula-II according to claim 2 further comprising purifying the (R)-2-(4-methanesulfonyl-3-methyl-pyridin-2-ylmethanesulfinyl)-1H-benzimidazole, wherein the process comprising:
    a) dissolving the (R)-2-(4-methanesulfonyl-3-methyl-pyridin-2-ylmethanesulfinyl)-1H-benzimidazole in a suitable solvent;
    b) optionally adding an antisolvent; and
    c) isolating pure (R)-2-(4-methanesulfonyl-3-methyl-pyridin-2-ylmethanesulfinyl)-1H-benzimidazole.

19. The process according to claim 18, wherein the solvent used in step a) is selected from water, ketones, nitriles, alcohol or mixtures thereof.

20. The process according to claim 18, wherein the solvent used in step a) is selected from water, acetone, methylethylketone, methylisobutylketone, acetonitrile, methanol, ethanol, isopropanol or mixtures thereof.

21. The process according to claim 18, wherein the antisolvent used in step b) is selected from water.

22. The process according to claim 2, wherein the oxidizing agent used in step a) is selected from a group consisting of metachloroperbenzoic acid, hydrogen peroxide, cumene hydroperoxide or sodium hypohalite.

23. The process according to claim 2, wherein the solvent used in step a) is selected from water, chlorinated aromatic or aliphatic hydrocarbons.

24. The process according to claim 2, wherein the chlorinating agent used in step b) is selected from thionylchloride, paratoluenesulfonyl chloride, methane sulfonyl chloride or ethane sulfonyl chloride, $POCl_3$, $PCl_5$ or oxalyl chloride.

25. The process according to claim 2, wherein the solvent used in step b) is selected from chloroform, dichloroethane, carbontetrachloride, benzene or toluene.

26. The process according to claim 2, wherein the base used in step c) is selected from sodium hydroxide, potassium hydroxide, barium hydroxide, sodium carbonate, potassium carbonate, cesium carbonate, sodium bicarbonate or potassium bicarbonate.

27. The process according to claim 2, wherein the stereoselective oxidation is carried out in the presence of an oxidizing agent selected from cumene hydrogen peroxide, metachloroperbenzoicacid, tert-butyl hydroperoxide, benzoyl peroxide, or sodium hypohalite.

28. The process according to claim 2, wherein the solvent used for stereoselective oxidation is selected from water, hydrocarbons, ethers, ketones, esters, nitriles or mixtures thereof.

29. The process according to claim 2, wherein the solvent used for stereoselective oxidation is selected from water, toluene, chloroform, dichloromethane, dichloroethane, tetrahydrofuran, acetone, methylethylketone, methylisobutylketone, ethylacetate, acetonitrile or mixtures thereof.

30. The process according to claim 2, wherein the base used for stereoselective oxidation is selected from the group of triethylamine, diisopropylamine, N,N-diisopropylethylamine, dicyclohexylamine, cyclohexylamine, tri-butylamine, n-butylamine or diisopropyl ethylamine.

31. The process according to claim 2, wherein the optically active reagent used for stereoselective oxidation is selected from enantiomerically pure mandelic acid, tartaric acid, diethyl tartaric acid, phenylethylamine, cinchonine, cinchonidine or brucine.

32. The process according to claim 2, wherein the metal catalyst used for stereoselective oxidation is selected from barium acetate, strontium acetate, titanium, vanadium, molybdenum or zirconium.

33. The process according to claim 2, wherein the base used in the substitution of benzimidazole sulphoxide is selected from sodium hydroxide, potassium hydroxide, sodium hydride, calcium hydroxide, barium hydroxide, magnesium hydroxide, sodium carbonate, potassium carbonate, cesium carbonate, sodium methoxide, sodium tertiary butoxide or potassium tertiary butoxide.

34. The process according to claim 2, wherein the solvent used in the substitution of benzimidazole sulphoxide is selected from dimethylsulfoxide, dimethylformamide, dimethyl acetate, N-methylpyrrolidone, methanol, ethanol, dioxane, toluene, xylene, tetrahydrofuran, dichloromethane acetonitrile, sulpholane or mixtures thereof.

* * * * *